United States Patent [19]

Kroneisen

[11] 4,202,748

[45] May 13, 1980

[54] ELECTROCHEMICAL MEASURING CELL

[75] Inventor: Armin Kroneisen, Frankfurt, Fed. Rep. of Germany

[73] Assignee: Hartmann & Braun AG., Frankfurt, Fed. Rep. of Germany

[21] Appl. No.: 928,058

[22] Filed: Jul. 26, 1978

[30] Foreign Application Priority Data

Jul. 27, 1977 [DE] Fed. Rep. of Germany ....... 2733781

[51] Int. Cl.² ........................................... G01N 27/46
[52] U.S. Cl. ............................... 204/195 R; 204/1 T
[58] Field of Search .......... 204/1 T, 1 K, 1 B, 195 R

[56] References Cited

U.S. PATENT DOCUMENTS

| 2,382,734 | 8/1945 | Marks | 204/1 B |
| 2,517,382 | 8/1950 | Brinker et al. | 204/195 R |
| 2,839,162 | 10/1974 | Ammer | 204/195 G |
| 3,470,071 | 9/1969 | Vertes et al. | 204/195 R |
| 3,480,520 | 11/1969 | Smith | 204/195 R |
| 3,681,228 | 8/1972 | Komidtr | 204/195 R |
| 3,707,455 | 12/1972 | Derr et al. | 204/195 P |
| 3,725,236 | 4/1973 | Johnson | 204/195 R |
| 4,049,503 | 9/1977 | Becker et al. | 204/195 R |

FOREIGN PATENT DOCUMENTS 2435813  2/1976  Fed. Rep. of Germany.
2436261  2/1976  Fed. Rep. of Germany.

Primary Examiner—T. Tung
Attorney, Agent, or Firm—Smyth, Pavitt, Siegemund, Jones & Martella

[57] ABSTRACT

The cell is filled with an electrolyte but partitioned into two chambers, one of which contains a particular additive which will react with a component of a fluid, e.g. air; no such reaction occurs in the other chamber. The two electrodes are similarly configured and both permit contact between the fluid and the electrolyte so that any other electrochemical reactions occur to a similar degree on both electrodes.

12 Claims, 2 Drawing Figures

ELECTROCHEMICAL MEASURING CELL

BACKGROUND OF THE INVENTION

The present invention relates to electrochemically measuring the concentration of fluid contaminants.

Measurements of the type to which the invention pertains is usually carried out by means of a measuring cell which contains two electrodes made of similar material and being in contact with an electrolyte. One of the electrodes is arranged and configured so that the fluid under examination can reach the phase boundary of the electrode and the electrolyte. An electrical signal can be taken from between the electrodes and information concerning the concentration of a particular component in that fluid can be derived from that signal.

An immediate problem arises involving cells of this type in that the cell may readily respond also to other components in the sample gas. In order to eliminate such a non-selectivity of the device one has used special filters which eliminate those additional components but permit passage of the component or contaminant to be detected. Such selective filters exhibit the drawback that inevitably they block also some of the compound to be measured. Moreover, such filter will rather rapidly saturate and have to be exchanged so that the maintenance of these devices is correspondingly extensive.

The German printed patent application No. 2,436,261 discloses an electrochemical measuring cell for various gaseous substances wherein blocking substances in the electorlyte impede any reaction with undesired components. The measuring gas flows past one of the two electrodes in the cell. The two electrodes are made of similar material.

The German printed patent application No. 2,435,813 discloses a measuring device whose selectivity results from an arrangement of different cells which respond differently to different compounds. The various electrical outputs are interconnected by a resistance network which produces a signal that in fact represents the concentration of the desired compound only, while the signals representing other compounds are suppressed.

DESCRIPTION OF THE INVENTION

It is an object of the present invention to provide a new and improved cell for electrochemically measuring components in fluids.

In accordance with the preferred embodiment of the present invention, it is suggested to provide a cell with two electrodes each of which being configured and arranged so that the fluid to be examined can reach the interfaces of the two electrodes with an electrolyte, but the environs of one electrode is provided with an additional substance which reacts only with the component to be detected. Moreover, separation means are provided to prevent the additive or auxiliary substance as well as the reaction products of that substance with the component to be detected from reaching the other electrode. However, these separate means may be constructed to permit electric current flow through the electrolyte. By way of example, phosphoric acid ester or phosgene (carbonyl chloride) in air has to be detected. In the first case one will use an oxime such as isonitrosobenzoylacetone; in the latter case, one will use alcohol, an amine, or water as additive.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Both cells shown in the two figures are destined to measure particular air pollutants. In FIG. 1 the cell is constructed from two coaxial tubular hanging parts 1 and 2 made of a plastic material such as PVC or polypropylene. The cell is to measure particularly phosphoric acid ester in air. The cell contains a watery solution of $NaHCO_3$ as electrolyte, but gelatine has been added to solidify the electrolyte.

Figure 1:
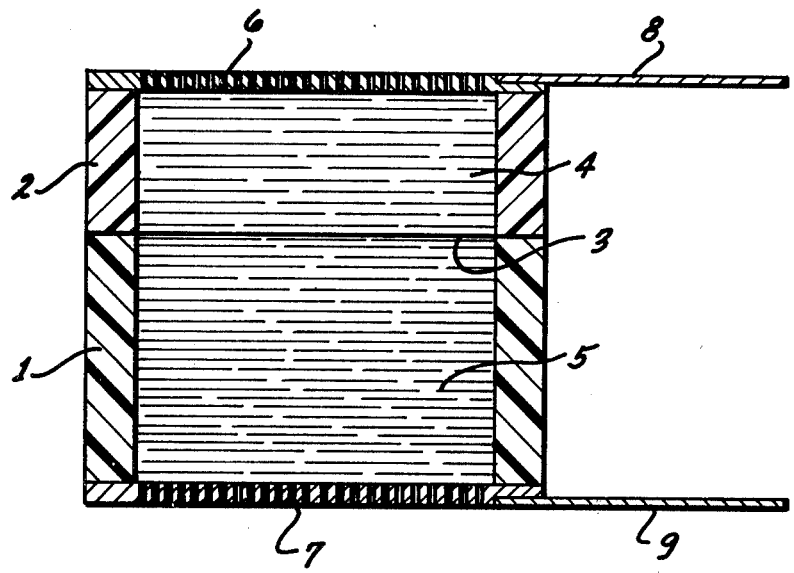
FIG. 1 is a schematic section view through a measuring cell in accordance with the preferred embodiment of the invention.

The tubes 1 and 2 respectively define chambers 5 and 4 each containing electrolyte, but the two chambers are separated by a diaphragm 3 made e.g. of plastic. The tubes and the diaphragm are interconnected by means of suitable adhesives to seal the two chambers off each other. The upper chamber 4 contains an additional substance, which in this instance may be iso-nitrosobenzoylacetone. This substance will not diffuse through the membrane. This is the principle requirement for such a membrane. The membrane may, however, permit ion exchange so that an electric current will flow that does not, however, depend on the migration of ions of the additive of chamber 4.

The cell is provided with two electrodes 6 and 7 made of an inert noble metal such as silver and having sieve-like configuration, i.e. they are provided with multiple apertures or perforations so that air can be admitted to both chambers to contact the electrolyte therein. The electrodes have inherently similar dimensions.

In operation, phosphoric acid ester in air to be measured as to concentration contacts the electrolyte through the two electrodes. A specific reaction occurs in chamber 4 with the isonitrosobenzoylacetone, resulting in an electrochemical reaction. A corresponding reaction does not take place in chamber 5 on account of the diaphragm 3 which retains the isonitrosobenzoylacetone in chamber 4.

The air contains other electrochemically active components such as $H_2S$, HCL, HCN, etc. Those components do not react with isonitrosobenzoylacetone. Thus, an electrochemical reaction of these additional air components occurs similarly at both electrodes so that any electrical difference signal attributible to these reactions is not produced. It can readily be seen that the two electrodes have identical configuration so that, in fact, any reaction attributable to other contaminants is of equal extensiveness and all electrical effects cancel. Any voltage between terminals 8 and 9 therefor is exclusively the result of the reaction at electrode 6 and of the absence of such a reaction at electrode 5.

Figure 2:
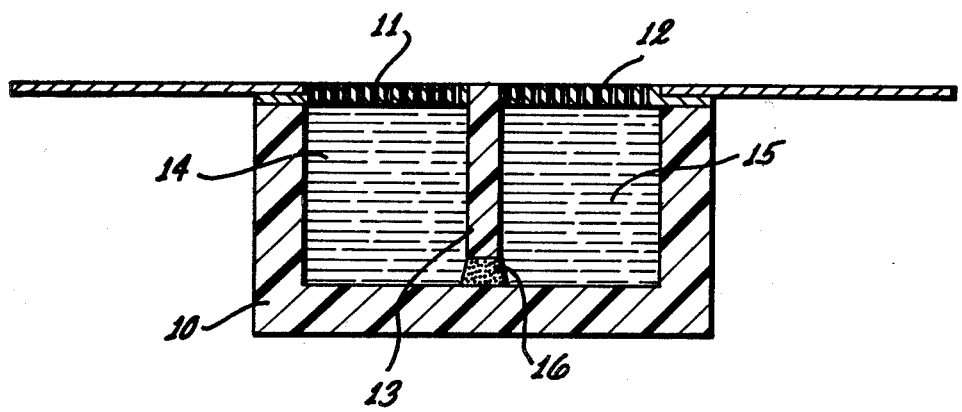
FIG. 2 is a similar view through a modified cell in accordance with the preferred embodiment.

In the case of a solidified electrolyte in which the auxiliary substance is embedded, it suffices to prevent ions of that substance to migrate to the other electrode. In FIG. 2, the cell is comprised of a single, pot-like container 10 and one half of the open top is covered by an electrode 11, the other half by an electrode 12. These electrodes are, therefor, similar half circles. However, a vertical partition 13 separates the two electrodes as well as the electrolyte in the container, defining accordingly two chambers 14 and 15.

Reference numeral 16 refers to a small, porous plug in an opening in that partition, or in a narrow gap between the partition and the bottom of the container. One of the chambers contains the additional or auxiliary substance, which will not migrate to the other chamber. Moreover, gaseous reaction products will not reach the bottom near portion of the chambers.

This cell may also be used to determine the content of phosphoric acid esters in air. Alternatively, both types of cells may be used to measure the content of phosgene in air. The additive in one of the chambers will be an alcohol, an amine, or water. In all instances, one will use about 0.1% to 50%, preferably 1% to 5% (by weight) of additive in the electrolyte, if pollutants are to be detected. The amount of additive needed depends to some extent on the expended concentration.

The invention is not limited to the embodiments described above but all changes and modifications thereof not constituting departures from the spirit and scope of the invention are intended to be included.

I claim:

1. An electrochemical measuring cell for measuring the content of a particular component in a fluid, comprising:
   container means;
   an electrolyte in the container means distinct from the fluid;
   a pair of electrodes made of similar metal and disposed on the container means to be in contact with the electrolyte therein, said electrodes being of perforated construction to permit said fluid to contact the electrolyte adjacent to the electrodes;
   an additive in the electrolyte selected for reacting only with the particular component and being disposed in the vicinity of only one of the electrodes; and
   barrier means disposed in the container separated from each electrode but in contact on each side with said electrolyte which separates the barrier means from the fluid external to the cell, for preventing the migration of the additive and of reaction products thereof with the particular component to the other one of the electrodes of the pair.

2. A cell as in claim 1, said barrier means for preventing being a diaphragm in the container.

3. A cell as in claim 2, said diaphragm being an ion exchange member.

4. A cell as in claim 2, said diaphragm being made of plastic.

5. A cell as in claim 1, said barrier means for preventing being a partition impermeable to ions, but having a small opening.

6. A cell as in claim 5, said opening being closed by a porous member.

7. A cell as in claim 1, said electrodes being made of a noble metal.

8. A cell as in claim 7, said electrodes being made of silver.

9. A cell as in claims 1, 7, or 8, said electrolyte in the container being a solidified gel.

10. A cell as in claim 9 for measuring the concentration of phosphoric acid ester in air, said additive being an oxime.

11. A cell as in claim 9 for measuring the concentration of phosphorous acid ester in air, said additive being isonitrosobenzoylacetone.

12. A cell as in claim 9 for measuring the concentration of phosgene in air, said additive being an alcohol, an amine or water.

* * * * *